US008021699B2

United States Patent
Yoshikawa et al.

(10) Patent No.: US 8,021,699 B2
(45) Date of Patent: Sep. 20, 2011

(54) GUAVA LEAF EXTRACT POWDER AND METHOD FOR PRODUCTION THEREOF

(75) Inventors: Masaki Yoshikawa, Minato-ku (JP); Tatsuyuki Kudo, Minato-ku (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 25 days.

(21) Appl. No.: 12/299,032

(22) PCT Filed: May 14, 2007

(86) PCT No.: PCT/JP2007/000511
§ 371 (c)(1),
(2), (4) Date: Oct. 30, 2008

(87) PCT Pub. No.: WO2007/135767
PCT Pub. Date: Nov. 29, 2007

(65) Prior Publication Data
US 2009/0087500 A1 Apr. 2, 2009

(30) Foreign Application Priority Data
May 18, 2006 (JP) .................................. 2006-138524

(51) Int. Cl.
*A61K 36/00* (2006.01)
(52) U.S. Cl. ........................................ 424/725; 424/774
(58) Field of Classification Search .......................... None
See application file for complete search history.

(56) References Cited

U.S. PATENT DOCUMENTS
6,713,093 B2   3/2004   Takahata et al.

FOREIGN PATENT DOCUMENTS

| EP | 1 262 543 A1 | | 12/2002 |
|---|---|---|---|
| JP | 60-56923 | | 4/1985 |
| JP | 63 251071 | | 10/1988 |
| JP | 4-311348 | | 11/1992 |
| JP | 6-269246 | | 9/1994 |
| JP | 7-59539 | | 3/1995 |
| JP | 7 59539 | | 3/1995 |
| JP | 09084565 A | * | 3/1997 |
| JP | 9-220053 | | 8/1997 |
| JP | 9 309840 | | 12/1997 |
| JP | 11-46737 | | 2/1999 |
| JP | 11-75770 | | 3/1999 |
| JP | 2000273048 A | * | 10/2000 |
| JP | 2003 208 | | 1/2003 |
| JP | 2004 57153 | | 2/2004 |
| JP | 2004 173504 | | 6/2004 |
| JP | 2006 50934 | | 2/2006 |
| WO | 2007 007732 | | 1/2007 |

OTHER PUBLICATIONS

Stricker, Freezing pharmaceuticals before lyophilization, Kaelte (Hamburg) (1970), 23 (10), 511-16.*
Deguchi, Y. et al., "Effects of Extract of Guave Leaves on the Development of Diabetes in the db/ db Mouse and on the Postprandial Blood Glucose of Human Subjects", Nippon Nogeikagaku Kaishi, vol. 72, No. 8, pp. 923-931, (1998).
Deguchi, Y.et al., "Effectiveness of Consecutive Ingestion and Excess Intake of Guava Leaves Tea in Human Volunteers", Journal of Japanese Council for Advanced Food Ingredients Research, vol. 3, No. 1, pp. 19-28, (2000).

* cited by examiner

*Primary Examiner* — Qiuwen Mi
(74) *Attorney, Agent, or Firm* — Oblon, Spivak, McClelland, Maier & Neustadt, L.L.P.

(57) ABSTRACT

The invention provides a method for producing a guava leaf extract powder, including extracting guava leaves with hot water at 90 to 98° C.; concentrating the obtained extract to a Brix level of 20 to 30; and lyophilizing the concentrated extract, and a guava leaf extract powder produced through the method which exhibits limited deterioration in quality after storage in solution for a long period of time.

16 Claims, No Drawings

GUAVA LEAF EXTRACT POWDER AND METHOD FOR PRODUCTION THEREOF

TECHNICAL FIELD

The present invention relates to a guava leaf extract powder which has excellent storage stability, is readily dissolved in water or hot water, exhibits excellent function after dissolution, and has stable quality, and to a method for producing the powder.

BACKGROUND ART

In recent years, the Japanese diet has changed, and occurrence of lifestyle-related diseases (both symptoms and signs thereof) such as hypertension, diabetes, brain infarction, and heart diseases has increased not only in the elder generation but also in the younger generation, posing serious problems. In many cases, such lifestyle-related diseases are pointed out to be closely related to obesity. Thus, treatment and prevention of obesity through improvement of diet and physical exercise are important for preventing lifestyle-related diseases.

The most common way to control diet is to limit calorie intake. However, this is not always a preferred method, since unavoidable changes in quantity and quality of diet are a painful burden, possibly causing stress. If conversion of ingested food into energy through metabolism in the living body is inhibited or delayed, calorie intake can be restricted without controlling diet, which is a painful task.

Hitherto, a substance inhibiting the activity of α-amylase, which is a hydrolase for starch as an energy source, has been considered effective for dieting. Therefore, extensive studies have been conducted on such substances, and a study has revealed that an extract produced from guava leaves possesses excellent α-amylase inhibitory activity (see Patent Document 1).

Guava (*Psidium guajava* L.) is a plant originating in tropical America and belonging to Myrtaceae and is grown in, for example, tropical regions, Taiwan, and Okinawa. The juice thereof is a very popular beverage. Guava leaf extract contains large amounts of polyphenol substances, tannin substances, saponin, ellagic acid glycosides, flavonoids, etc., and a study revealed that the extract exhibits, in addition to the aforementioned α-amylase inhibitory activity, an effect of inhibiting formation of lipid peroxide (see Patent Document 2). There has been proposed use of guava leaf extract as an ingredient of foods and beverages.

However, when a guava leaf extract is stored for a long period of time, polyphenol substances and other ingredients make the extract cloudy, or form precipitates. Thus, when a beverage or the like containing such a guava leaf extract is charged into a container, the appearance of the beverage product is impaired, in some cases lowering motivation of consumers for purchasing the product.

In general, methods for maintaining quality of a plant extract containing large amounts of polyphenols and tannins have been reported. For example, filtration through diatomaceous earth (see Patent Document 3), removal of polyphenols with adsorbing resin (see Patent Document 4), and decomposition of tannins by use of tannase (see Patent Document 5) have been reported. Through performing these processes, some ingredients of guava leaf extract can be removed. However, since some of the removed ingredients are thought to be related to advantageous functions of guava, such conventionally employed treatments are not necessarily preferable. From another aspect, there has been proposed an approach for producing a guava leaf extract suitable for long-term storage, including incorporating stevia into the extract (see Patent Document 6). However, use of an additive should be avoided to the greatest extent.

Patent Document 1: JP-B-2670742
Patent Document 2: JP-A-1999-75770
Patent Document 3: JP-A-1992-311348
Patent Document 4: JP-A-1997-220053
Patent Document 5: JP-A-1994-269246
Patent Document 6: JP-A-1999-46737

DISCLOSURE OF THE INVENTION

Problems to be Solved by the Invention

Thus, an object of the present invention is to provide a guava leaf extract powder which exhibits no deterioration in quality and functions after storage for a long period of time and which is excellent in taste and quality after re-dissolution in water or hot water. Another object of the invention is to provide a food containing the powder.

Means for Solving the Problems

The present inventors have conducted extensive studies in order to solve the aforementioned problems, and have found that, through extracting guava leaves with hot water at 90 to 98° C., concentrating the extract to a Brix level of 20 to 30, and lyophilizing the concentrated extract, there can be produced a guava leaf extract powder which exhibits no deterioration in quality and functions after storage for a long period of time and which can be readily re-dissolved in water or hot water, to thereby provide a beverage excellent in taste, quality, and stability. The present invention has been accomplished on the basis of this finding.

Accordingly, the present invention provides a method for producing a guava leaf extract powder, comprising:
(A) extracting guava leaves with hot water at 90 to 98° C., to thereby produce an extract;
(B) concentrating the extract to a Brix level of 20 to 30, to thereby form a concentrated extract; and
(C) lyophilizing the concentrated extract.

The present invention also provides a guava leaf extract powder produced through the method for producing a guava leaf extract powder, and a food or a beverage containing the guava leaf extract powder.

Effects of the Invention

The guava leaf extract powder produced through the method of the present invention exhibits less deterioration in quality and functions of the guava leaf extract after storage for a long period of time. In addition, when the guava leaf extract powder is re-dissolved in water or hot water, the solution forms only a small amount of precipitates, and a guava leaf flavor is maintained without deterioration.

BEST MODES FOR CARRYING OUT THE INVENTION

The method of the present invention for producing a guava leaf extract powder, includes the steps (A) to (C):
(A) extracting guava leaves with hot water at 90 to 98° C., to thereby produce an extract;
(B) concentrating the extract to a Brix level of 20 to 30, to thereby form a concentrated extract; and (C) lyophilizing the concentrated extract. These steps will next be described in detail.

In step (A); i.e., preparation of a guava leaf extract, guava leaves employed as a raw material may be fresh leaves. However, in consideration of extraction efficiency for effective ingredients and other factors, dry leaves and broken leaves thereof are preferably employed. Furthermore, for enhancing the taste, dried and roasted guava leaves may be employed. When broken leaves are used, broken fragments preferably have a dimension of 1 mm to 10 mm, particularly preferably an average dimension of 3 to 5 mm.

Extraction of guava leaves may be performed with an aqueous solvent. Examples of the aqueous solvent include water, ethanol, and acetone. From the viewpoint of, for example, safety, the guava leaf extract powder produced through the steps described hereinbelow for use in food, preferably employs water or a water-ethanol solvent mixture. The amount of extraction solvent is 10 to 40 parts by weight with respect to 1 part by weight of guava leaves, more preferably 15 to 25 parts by weight. When the amount of extraction solvent is less than 10 parts by weight, extraction efficiency may decrease, whereas when the amount is in excess of 40 parts by weight, the efficiency of the concentration step mentioned hereinbelow may decrease.

When guava leaves are extracted with the aforementioned extraction solvent, the extraction temperature is 90 to 98° C., particularly preferably 93 to 97° C. When the extraction temperature is lower than 90° C., sufficient extraction of guava leaves may fail to be attained, whereas when the extraction temperature is higher than 98° C., extracted effective ingredients are deteriorated, to thereby increase the amount of precipitation after re-dissolution in water or hot water. The extraction time is preferably 3 to 30 minutes.

Next, in step (B); i.e., the concentration step, the guava leaf extract produced in step (A) is concentrated through a routine method. Preferably, the guava leaf extract is concentrated to a Brix level of about 20 to about 30, more preferably about 23 to about 28. When the concentrated guava leaf extract has a Brix level less than 20, lyophilization efficiency may decrease, whereas when the Brix level is in excess of 30, a large amount of precipitates may form in the guava leaf extract. The concentration may be performed by means of a known concentration apparatus such as an evaporator. No particular limitation is imposed on the concentration conditions, and the concentration is preferably performed at 25 to 70° C. under a vacuum of 0 to 48 kPa, from the viewpoints of, for example, prevention of deterioration of flavor and effective ingredients.

Subsequently, the concentrated guava leaf extract prepared in step (B) is lyophilized in step (C), to thereby pulverize the extract. In step (C), the concentrated guava leaf extract obtained in step (B) is lyophilized through a known technique. In one preferred embodiment, the concentrated extract is cooled to −20° C. to −50° C., and heat is supplied to the cooled extract under reduced pressure (4 Pa to 107 Pa) so that the temperature of the dried product finally reaches 60° C. or lower. For pulverization, spray-drying is one known method. However, when the concentrated guava leaf extract is pulverized by such a known method, the obtained powder has intense oxidized odor, which is not preferred in terms of flavor.

Before lyophilization of the concentrated extract performed in step (C), preliminary freezing at −20 to −50° C. for 10 hours or longer is preferably performed, from the viewpoint of stability of effective ingredients. In a preferred embodiment, the preliminary freezing is performed at −20 to −50° C., more preferably −35 to −40° C., and for at least 10 hours, more preferably 15 to 30 hours, from the viewpoint of stability of effective ingredients and solubility of the powder in water.

The thus-produced guava leaf extract powder is very stable in quality for a long storage period and satisfactorily maintains functions thereof. In addition, the powder has very high solubility in water or hot water. Therefore, the powder of the present invention can be used not only as conventional health-promoting food and nutrient supplements in the form of pellet, tablet, granule, capsule, etc., but also as a material for producing beverages such as portable instant beverages and tea drinks. Also, the guava leaf extract powder has excellent storage stability after dissolution in water or hot water, forms only a small amount of precipitation, and is tasty.

The guava leaf extract powder of the invention may also find a variety of food/beverage uses, in combination of side materials, including dairy products such as milk, cream, cheese, and butter; fermented milk products; lactobacillus beverages; yoghurt; dressing; processed meat products such as ham and sausage; processed fish products such as kamaboko and chikuwa; bread; and confectioneries. The amount of guava leaf extract powder used in such a food/beverage product depends on the form of the product and may be predetermined as appropriate. The amount is generally 0.10 wt. % to 1.50 wt. % with respect to the total amount of the product, preferably 0.15 wt. % to 1.25 wt. %. Notably, in addition to food/beverage products, the guava leaf extract powder of the present invention may be used as an ingredient of cosmetics, pharmaceuticals, etc.

When the powder of the invention is granulated, no particular limitation is imposed on the granulation method. Preferably, for the purpose of improving stability, adhesion, dispersibility, and fluidity of effective ingredients, granulation is performed through fluidized-bed granulation, extrusion granulation, etc. No particular limitation is imposed on the binder employed in granulation, and pullulan, starch, dextrin, hydroxypropylmethyl cellulose, etc. may be employed.

EXAMPLES

The present invention will next be described in more detail by way of examples, which should not be construed as limiting the invention thereto.

Example 1

Dry guava leaves (about 80 kg) were immersed in hot water (95° C., 1,600 kg), and extraction was performed under stirring for 15 minutes. The product was filtered by means of a 150-mesh filter, and the obtained liquid was cooled to 30° C. or lower and centrifuged, to thereby remove impurities. The thus-obtained extract was concentrated at 60° C. under a vacuum of 21 kPa, whereby a concentrated extract having a Brix level of 25 was yielded. The concentrated extract was preliminarily frozen at −40° C. for 15 hours and, subsequently, lyophilized at 67 Pa, whereby a brown guava leaf extract powder was yielded.

The thus-produced guava leaf extract powder was good in flavor with only a low level of oxidized odor and had a high active ingredient content. The powder had excellent solubility in water.

Example 2

Food Containing Guava Leaf Extract Powder

Ingredients shown in Table 1 were placed in a blender and agitated for 10 minutes. The resultant mixture was removed from the blender and pelletized by means of a direct pelletizer, to thereby produce pellets thereof (diameter: 8 mm, weight 200 mg). The thus-produced pellets exhibited excellent elution and disintegration properties in water and gave an excellent score in a friability test.

TABLE 1

| Raw materials | Content |
| --- | --- |
| Guava leaf extract powder produced in Example 1 | 120 mg |
| Palatinit | 75.6 mg |
| Sucrose fatty acid ester | 4 mg |
| Sucralose | 0.4 mg |

Example 3

Production of Guava Tea Beverage

The guava leaf extract powder produced in Example 1 was dissolved in water so that the Brix level of the solution was adjusted to 0.25. Sodium ascorbate (0.03%) was added to the solution, and the pH of the resultant liquid was adjusted to 6.0 with sodium bicarbonate, followed by stirring for 10 minutes. The blended liquid was heated at 135° C. for one minute by means of a tube-type sterilizer and cooled to 85° C. The liquid was charged into a 500-mL PET bottle and cooled to 40° C. or lower (Invention Product 1).

Comparative Example 1

Dry guava leaves (about 80 kg) were immersed in hot water (95° C., 1,600 kg), and extraction was performed under stirring for 15 minutes. The product was filtered by means of a 150-mesh filter, and the obtained liquid was cooled to 30° C. or lower and centrifuged, to thereby remove impurities. The thus-obtained extract was concentrated at 60° C. under a vacuum of 21 kPa, whereby a concentrated extract having a Brix level of 25 was yielded. The concentrated extract was pulverized by means of a spray-drier, whereby a brown guava leaf extract powder was yielded. The guava leaf extract powder was dissolved in water so that the Brix level of the solution was adjusted to 0.25. Sodium ascorbate (0.03%) was added to the solution, and the pH of the resultant liquid was adjusted to 6.0 with sodium bicarbonate, followed by stirring for 10 minutes. The blended liquid was heated at 135° C. for one minute by means of a tube-type sterilizer and cooled to 85° C. The liquid was charged into a 500-mL PET bottle and cooled to 40° C. or lower (Comparative Product 1).

Comparative Example 2

Dry guava leaves (about 80 kg) were immersed in hot water (95° C., 1,600 kg), and extraction was performed under stirring for 15 minutes. The product was filtered by means of a 150-mesh filter, and the obtained liquid was cooled to 30° C. or lower and centrifuged, to thereby remove impurities. The thus-obtained extract was concentrated at 60° C. under a vacuum of 21 kPa, whereby a concentrated extract having a Brix level of 25 was yielded. The concentrated extract was heated to evaporate water, to thereby produce a paste-like, high-concentration extract having a Brix level of 65. The high-concentration guava leaf extract was dissolved in water so that the Brix level of the solution was adjusted to 0.25. Sodium ascorbate (0.03%) was added to the solution, and the pH of the resultant liquid was adjusted to 6.0 with sodium bicarbonate, followed by stirring for 10 minutes. The blended liquid was heated at 135° C. for one minute by means of a tube-type sterilizer and cooled to 85° C. The liquid was charged into a 500-mL PET bottle and cooled to 40° C. or lower (Comparative Product 2).

Comparative Example 3

Dry guava leaves (about 80 kg) were immersed in hot water (1,600 kg), and extraction was performed at 120° C. by means of a pressure-type extraction pot for 15 minutes. The product was filtered by means of a 150-mesh filter, and the obtained liquid was cooled to 30° C. or lower and centrifuged, to thereby remove impurities. The thus-obtained extract was concentrated at 60° C. under a vacuum of 21 kPa, whereby a concentrated extract having a Brix level of 25 was yielded. The concentrated extract was preliminarily frozen at −40° C. for 15 hours and, subsequently, lyophilized at 67 Pa, whereby a brown guava leaf extract powder was yielded. The guava leaf extract powder was dissolved in water so that the Brix level of the solution was adjusted to 0.25. Sodium ascorbate (0.03%) was added to the solution, and the pH of the resultant liquid was adjusted to 6.0 with sodium bicarbonate, followed by stirring for 10 minutes. The blended liquid was heated at 135° C. for one minute by means of a tube-type sterilizer and cooled to 85° C. The liquid was charged into a 500-mL PET bottle and cooled to 40° C. or lower (Comparative Product 3).

Test Example 1

The flavor of each of the guava tea beverages produced in Example 3 and Comparative Examples 1, 2, and 3 (Invention Product 1 and Comparative Products 1 to 3) was checked. Separately, these beverage products were stored at 37° C. for one month during which each product was placed in a PET bottle, and the amount of precipitated matter deposited on the bottom of the bottle was determined. For determining the precipitation amount, each guava tea beverage (500 mL, equivalent to the volume of one bottle) was filtered through a 3-μm membrane filter, and the precipitated matter captured by the membrane filter was weighed. The results are shown in Table 2.

TABLE 2

| Guava tea beverage | Flavor | Precipitation amount (mg/bottle) |
| --- | --- | --- |
| Invention Product 1 | Characteristic guava flavor. Easy to drink. | 8.1 |
| Comparative Product 1 | Oxidized odor. Difficult to to drink. | 9.8 |
| Comparative Product 2 | Characteristic guava flavor. Easy to drink. | 16.2 |
| Comparative Product 3 | Characteristic guava flavor. Easy to drink. | 10.9 |

As is clear from Table 2, by use of a guava leaf extract powder produced through lyophilization under the conditions of Example 1, there can be provided a guava tea beverage which is tasty and which generates only a small amount of deposits on the bottom of a bottle during storage.

INDUSTRIAL APPLICABILITY

The guava leaf extract powder produced through the method of the present invention exhibits less deterioration in quality and functions intrinsic to the guava leaf extract after storage for a long period of time. The powder of the present invention is readily re-dissolved in water or hot water, and the storage stability of the solution is satisfactory. Therefore, a beverage containing a guava leaf extract can be readily produced in a simple manner from the guava leaf extract powder of the present invention. The powder of the invention is a useful material for portable instant beverages and the like and is suitable for long-distance transportation.

The invention claimed is:

1. A method for producing a guava leaf extract powder, comprising:
   (A) extracting guava leaves with hot water at 90 to 98° C., to thereby produce an extract;
   (B) concentrating the extract to a Brix level of 20 to 30, to thereby form a concentrated extract;
   (C) performing preliminary freezing of the concentrated extract at −20 to −50° C. for 10 hours or longer; and
   (D) lyophilizing the concentrated extract after preliminary freezing of the concentrated extract is performed,
   wherein when the guava leaf extract powder is used to form a beverage and the beverage is stored at 37° C. for one month in a 500 ml bottle, 8.1 mg or less of deposits are formed in the bottle as captured using a 3-μm filter.

2. A guava leaf extract powder produced through the method according to claim 1.

3. A food or a beverage containing the guava leaf extract powder according to claim 2.

4. The method for producing a guava leaf extract powder according to claim 1, wherein the guava leaves are dry leaves.

5. The method for producing a guava leaf extract powder according to claim 4, wherein the dry leaves are roasted.

6. The method for producing a guava leaf extract powder according to claim 4, wherein the dry leaves are broken and have a dimension of 1 mm to 10 mm.

7. The method for producing a guava leaf extract powder according to claim 6, wherein the dry leaves are broken and have a dimension of 3 mm to 5 mm.

8. The method for producing a guava leaf extract powder according to claim 1, wherein an amount of extraction solvent is 10 to 40 parts by weight with respect to 1 part by weight of the guava leaves.

9. The method for producing a guava leaf extract powder according to claim 8, wherein the amount of extraction solvent is 15 to 25 parts by weight with respect to 1 part by weight of the guava leaves.

10. The method for producing a guava leaf extract powder according to claim 1, wherein the hot water has a temperature between 93° C. to 97° C.

11. The method for producing a guava leaf extract powder according to claim 1, wherein extracting guava leaves with hot water takes place for 3 to 30 minutes.

12. The method for producing a guava leaf extract powder according to claim 1, wherein the extract is concentrated to a Brix level of 23 to 28.

13. The method for producing a guava leaf extract powder according to claim 1, wherein concentrating the extract is performed at 25° C. to 70° C. under a vacuum of 0 kPa to 48 kPa.

14. The method for producing a guava leaf extract powder according to claim 1, wherein the preliminary freezing is performed at −35° C. to −40° C.

15. The method for producing a guava leaf extract powder according to claim 14, wherein the preliminary freezing is performed for 15 to 30 hours.

16. A method for producing a guava leaf extract powder, consisting essentially of:
   (A) extracting guava leaves with hot water at 90 to 98° C., to thereby produce an extract;
   (B) concentrating the extract to a Brix level of 20 to 30, to thereby form a concentrated extract; and
   (C) performing preliminary freezing of the concentrated extract at −20 to −50° C. for 10 hours or longer; and
   (D) lyophilizing the concentrated extract after preliminary freezing of the concentrated extract is performed,
   wherein when the guava leaf extract powder is used to form a beverage and the beverage is stored at 37° C. for one month in a 500 ml bottle, 8.1 mg or less of deposits are formed in the bottle as captured using a 3-μm filter.

* * * * *